US012589107B2

(12) United States Patent
Zhou et al.

(10) Patent No.: US 12,589,107 B2
(45) Date of Patent: Mar. 31, 2026

(54) COMPOSITION CONTAINING NICOTINAMIDE MONONUCLEOTIDE AND MOGROSIDE, AND APPLICATION THEREOF

(71) Applicants: Beijing Hebabiz Biotechnology Co., Inc., Beijing (CN); Beijing Hebabiz Management Co., Ltd., Beijing (CN)

(72) Inventors: James Zhou, Westport, CT (US); Bai-Bo Xie, Beijing (CN); Xinyu Zang, Beijing (CN)

(73) Assignees: Beijing Hebabiz Biotechnology Co., Inc., Beijing (CN); Beijing Hebabiz Management Co., Ltd., Beijing (CN)

( * ) Notice: Subject to any disclaimer, the term of this patent is extended or adjusted under 35 U.S.C. 154(b) by 1106 days.

(21) Appl. No.: 17/435,211

(22) PCT Filed: Mar. 14, 2019

(86) PCT No.: PCT/CN2019/078155
§ 371 (c)(1),
(2) Date: Aug. 31, 2021

(87) PCT Pub. No.: WO2020/177153
PCT Pub. Date: Sep. 10, 2020

(65) Prior Publication Data
US 2022/0133763 A1 May 5, 2022

(30) Foreign Application Priority Data
Mar. 1, 2019 (CN) .......................... 201910156573.6

(51) Int. Cl.
*A61K 31/706* (2006.01)
*A23L 2/38* (2021.01)
(Continued)

(52) U.S. Cl.
CPC .............. *A61K 31/706* (2013.01); *A23L 2/38* (2013.01); *A23L 33/105* (2016.08); *A23L 33/13* (2016.08); *A61K 31/455* (2013.01); *A61K 31/704* (2013.01)

(58) Field of Classification Search
CPC .. A61K 31/706; A61K 31/455; A61K 31/704; A23L 33/105; A23L 33/13
See application file for complete search history.

(56) References Cited

U.S. PATENT DOCUMENTS

2007/0082373 A1 4/2007 Imai et al.
2007/0082837 A1 4/2007 Bajgrowicz

FOREIGN PATENT DOCUMENTS

CN 105560258 A 5/2016
JP 2018203691 A 12/2018
(Continued)

OTHER PUBLICATIONS

Mills et al. "Long-term administration of nicotinamide mononucleotide mitigates age-associated physiological decline in mice." Cell metabolism 24.6 (2016): 795-806. (Year: 2016).*

(Continued)

*Primary Examiner* — Joseph K McKane
*Assistant Examiner* — Ashli Ariana Chicks
(74) *Attorney, Agent, or Firm* — Bachman & LaPointe, P.C.

(57) ABSTRACT

The present invention belongs to the medical and technical field and provides a medicine or health food composition of nicotinamide mononucleotide and mogroside. In addition, the present invention also provides the preparation method, formulation and application of the composition.

17 Claims, 5 Drawing Sheets

(51) Int. Cl.

| | |
|---|---|
| *A23L 33/105* | (2016.01) |
| *A23L 33/13* | (2016.01) |
| *A61K 31/455* | (2006.01) |
| *A61K 31/704* | (2006.01) |

(56) References Cited

FOREIGN PATENT DOCUMENTS

| | | | |
|---|---|---|---|
| WO | 2014146033 A1 | 9/2014 | |
| WO | 2014146044 A1 | 9/2014 | |
| WO | 2019002858 A1 | 1/2019 | |
| WO | WO-2020106746 A1 * | 5/2020 | ......... A61K 31/7084 |

OTHER PUBLICATIONS

Di et al. Journal of Agricultural and Food Chemistry 2011 59 (13), 7474-7481. (Year: 2011).*

Chou, T.C., Leukemia & Lymphoma 2008, 49, 2059-2080. (Year: 2008).*

Chou, T.C., Cancer Res., 2010, 70(2), 440-446. (Year: 2010).*

Office Action dated Jul. 31, 2023 for corresponding application JP2021-551908.

Qi et al., Mogrosides extract from Siraitia grosvenori scavenges free radicals in vitro and lowers oxidative stress, serum glucose, and lipid levels in alloxan-induced diabetic mice, Nutrition Research, Feb. 5, 2008, vol. 28, pp. 278-284, doi: 10.1016/j.nutres.2008.02.008.

Zhang et al., Effects of Mogrosides on High-Fat-Diet-Induced Obesity and Nonalcoholic Fatty Liver Disease in Mice, Molecules, Jul. 29, 2018, vol. 23, 1894, pp. 1-11, doi: 10.3390/molecules23081894.

International search report for patent application No. PCT/CN2019/078155 dated Oct. 14, 2019.

* cited by examiner

COMPOSITION CONTAINING NICOTINAMIDE MONONUCLEOTIDE AND MOGROSIDE, AND APPLICATION THEREOF

TECHNICAL FIELD

The present invention belongs to the medical and technical field. Specifically, the present invention provides a composition containing nicotinamide mononucleotide and mogroside for inhibiting the growth of adipocytes and/or promoting the viability of islet cells.

BACKGROUND OF THE INVENTION

Disorders of glucose and lipid metabolism in the human body cause pancreatic islet cell damage and insulin resistance, promote adipocyte growth and fat accumulation, and lead to obesity, hyperlipidemia, hyperglycemia, and cardiovascular diseases, such as vascular sclerosis. Therefore, effective control of adipocyte reproduction, growth and islet cell damage has important health significance for obesity, hyperlipidemia, hyperglycemia, cardiovascular disease, and even the length of life. At present, there are thousands of compounds and extracts for obesity, hyperlipidemia and hyperglycemia, as well as corresponding drugs and health foods on the market.

β-nicotinamide mononucleotide (abbreviated as NMN) is the most direct precursor of coenzyme I (NAD+). Although it has been reported that NMN can promote glucose-induced insulin secretion, it has no obvious effect on promoting the growth of islet cells or resisting islet cell damage (Spinnler R. et al., PLOS ONE January 2013, 2.7). Chinese patent applications CN106715455A and CN106536535A instead studied and prepared analogs of nicotinamide riboside for the treatment of diseases that benefit from increased NAD levels, including mitochondrial diseases, insulin resistance, metabolic syndrome, diabetes, and obesity etc. In addition, the manufacturing cost of NMN is high (market price of RMB 200-20,000/g), and the anti-aging effect currently confirmed is large (0.6-2 g/person/day), and the cost of use is as high as several tens of thousands to millions per person per year, directly affecting the promotion and application.

Mogroside (abbreviated as MG) has been mainly used as a substitute for sucrose in recent years. Chinese patent application CN105640971 A discloses the application of total saponins in immature Corsvenor Momordica Fruit extract in the preparation of auxiliary hypoglycemic drugs. Among them, mogroside II, mogroside III and their combination can inhibit α-glucosidase activity in vitro and in vivo, reduce the fasting blood glucose and postprandial blood glucose levels of type II diabetic mice, and reduce the insulin resistance index; and Chinese patent application CN108201546 A discloses the application of Corsvenor Momordica Fruit preparation in the preparation of medicines for the treatment of fatty liver, among which, Corsvenor Momordica Fruit water extract and Mogroside V (referred to as MGV) can effectively reduce the accumulation of liver triglycerides by reducing endoplasmic reticulum stress-related proteins and the expression of fat synthesis-related genes for the treatment of fatty liver. However, there are also reports that mogroside has some protective effects on pancreatic islet cells through antioxidant effects, but the effect is weak, and there is no clear evidence for inhibiting the growth of adipocytes and negatively regulating fat accumulation in cells (Chen Shanyuan et al., China Pharmacy 2012, Vol. 0.23 No 0.23). Therefore, in the prior art, there is still some controversy about the effects of nicotinamide mononucleotide and mogroside in inhibiting the growth of adipocytes and promoting the viability of pancreatic islet cells. It is difficult to determine both of these from the thousands of compounds and extracts for obesity, hyperlipidemia, and hyperglycemia. However, based on the accumulated experience of long-term research, the inventors used NMN and MG together, and surprisingly discovered that the combination of the two has unexpected synergistic effects in blood glucose control, protection of islet cells, inhibition of fat cell growth and fat accumulation etc. Moreover, in the composition of the present invention, a relatively low-cost MG can be used to replace a considerable portion of the expensive NMN to achieve the same or similar effects, thereby significantly reducing the cost and making it more suitable for promotion.

SUMMARY OF THE INVENTION

The technical problem to be solved by the present invention is to provide a new medicine or health food composition for inhibiting the growth of adipocytes and/or promoting the viability of pancreatic islet cells. The present invention also provides the preparation method of the pharmaceutical preparation or health food composition, the corresponding pharmaceutical preparation or health food and application etc.

Specifically, in the first aspect, the present invention provides a pharmaceutical composition or a health food composition, which comprises nicotinamide mononucleotide and mogroside. That is, the present invention provides a pharmaceutical composition comprising nicotinamide mononucleotide and mogroside; or, the present invention provides a health food composition comprising nicotinamide mononucleotide and mogroside.

In this context, a pharmaceutical composition refers to a composition with medical activity used to formulate a medicine or drug product. In this context, the health food composition refers to a composition with health care functions used to formulate health food.

In the specific embodiment of the present invention, the pharmaceutical composition or health food composition of the first aspect of the present invention only uses nicotinamide mononucleotide and mogroside as the pharmacologically active or health-care active ingredients, so preferably, the pharmaceutical composition or health food composition of the first aspect of the present invention consists of nicotinamide mononucleotide and mogroside.

Preferably, in the pharmaceutical composition or health food composition of the first aspect of the present invention, the molar ratio of nicotinamide mononucleotide:mogroside is 1-100:0.1-1000, preferably 1-10:0. 1-100, more preferably 1-5:1-30; for example, 1-2:1-5.

The inventors discovered that mogroside V in mogroside is mainly responsible, so preferably, mogroside is mogroside V in the pharmaceutical composition or health food composition of the first aspect of the present invention. However, the present inventor found that the Corsvenor Momordica Fruit extract with high mogroside V content can basically be used instead of mogroside V, thereby saving costs. Therefore, preferably, in the pharmaceutical composition or health food composition of the first aspect of the present invention, mogroside is a Corsvenor Momordica Fruit extract containing mogroside V, and preferably, the content of mogroside V in the said extract is not less than 30% (w/w), more preferably, not less than 60% (w/w).

When mogroside is a Corsvenor Momordica Fruit extract containing mogroside V, preferably, the method for extracting mogroside includes the following steps:

(1) Corsvenor Momordica Fruit is extracted by heating with water and filtered;

(2) The filtrate obtained in step (1) is purified with a D101 macroporous resin chromatography column, and the eluent eluted with 35-45% (V/V) ethanol is collected and concentrated; and (3) The concentrated solution obtained in step (2) is purified with an ADS-7 macroporous resin chromatography column, and the eluate eluted with 25-35% (V/V) ethanol is collected and concentrated to dryness.

In the second aspect, the present invention provides a method for preparing the pharmaceutical composition or health food composition of the first aspect of the present invention, which includes the step of mixing nicotinamide mononucleotide and mogroside.

When mogroside is a Corsvenor Momordica Fruit extract containing mogroside V, it is preferable that the preparation method of the second aspect of the present invention includes an extraction method for mogroside, and the said extraction method will be implemented before the step of mixing nicotinamide mononucleotide and mogroside.

More preferably, in the preparation method of the second aspect of the present invention, the extraction method includes the following steps:

(1) Corsvenor Momordica Fruit is extracted by heating with water and filtered;

(2) The filtrate obtained in step (1) is purified with a D101 macroporous resin chromatography column, and the eluent eluted with 35-45% (V/V) ethanol is collected and concentrated; and (3) The concentrated solution obtained in step (2) is purified with an ADS-7 macroporous resin chromatography column, and the eluate eluted with 25-35% (V/V) ethanol is collected and concentrated to dryness.

In the third aspect, the present invention provides a pharmaceutical preparation or health food, which includes the pharmaceutical composition or health food composition of the first aspect of the present invention, and pharmaceutically or food acceptable excipients. That is, the present invention provides a pharmaceutical preparation, which includes the pharmaceutical composition of the first aspect of the present invention, and pharmaceutically acceptable excipients; or, the present invention provides a health food, which includes the health food composition of the first aspect of the present invention, and food acceptable excipients.

As used herein, the term "pharmaceutically acceptable excipients" includes pharmaceutically acceptable carriers, excipients, diluents, etc., which are compatible with the active pharmaceutical ingredients. The use of pharmaceutically acceptable excipients to prepare pharmaceutical preparations is well known to those of ordinary skill in the art. The pharmaceutical preparation of the present invention comprises the pharmaceutical composition of the first aspect of the present invention as an active ingredient, and the composition and pharmaceutically acceptable excipients (such as carriers, excipients, diluents, etc. well known to those of ordinary skill in the art) are combined together and formulated into various preparations, preferably solid preparations and liquid preparations, such as tablets, pills, capsules (including sustained release or delayed release forms), powders, suspensions, granules, syrups, emulsions, suspension liquids and other dosage forms, and various sustained-release dosage forms, preferably in the form of oral administration.

In this context, the term "food acceptable excipients" includes food acceptable carriers, excipients, diluents, flavoring agents, coloring agents, fumettes, etc., which are compatible with food health active ingredients. The health food composition of the first aspect of the present invention can directly constitute food or food raw materials, or can be added to food or food raw materials, for example, can coat the surface of other foods, or can be mixed with other foods.

Preferably, the pharmaceutical preparations or health foods of the third aspect of the present invention are milk products, beverages, biscuits or granules. Among them, the first three are usually specific food forms of health foods, and the latter are usually specific preparation forms of pharmaceutical preparations.

In the fourth aspect, the present invention provides the application of pharmaceutical composition or health food composition of the first aspect of the present invention in the preparation of pharmaceutical preparations for reducing blood glucose, promoting the growth and repair of islet cells, preventing and treating hyperglycemia, and/or preventing and treating diabetes. Accordingly, in the fifth aspect, the present invention provides a method for lowering blood glucose, promoting the growth and repair of islet cells, preventing and treating hyperglycemia, and/or preventing and treating diabetes, which includes administering the pharmaceutical composition of the first aspect of the present invention to an individual in need.

In the sixth aspect, the present invention provides the application of the pharmaceutical composition of the first aspect of the present invention in the preparation of pharmaceutical preparations for controlling fat accumulation and weight, preventing and treating hyperlipidemia, and/or preventing and treating cardiovascular diseases. Correspondingly, in the seventh aspect, the present invention provides a method for controlling fat accumulation and body weight, preventing and treating hyperlipidemia, and/or preventing and treating cardiovascular diseases, which comprises administering the pharmaceutical composition of the first aspect of the present invention to individuals in need.

In the specific embodiment of the present invention, when used in the human body to control blood glucose and body weight, the dose based on nicotinamide mononucleotide is usually 100-300 mg/day, which is much smaller than the amount of nicotinamide mononucleotide used alone. (500-2000 mg/day).

The beneficial effect of the present invention is that it is found that the combination of NMN and MG can synergistically benefit blood glucose control, protect islet cells, inhibit adipocyte growth and fat accumulation, etc., and replace a considerable part of the expensive NMN with MG with lower cost to achieve the same or similar effect, thus significantly reducing the cost and more suitable for promotion.

To facilitate understanding, the present invention will be described in detail below through specific embodiments. It should be particularly pointed out that these descriptions are merely exemplary descriptions and do not constitute a limitation on the scope of the present invention. Based on the description of this specification, many changes and modifications of the present invention are obvious to those skilled in the art.

In addition, the present invention cites published literatures for the purpose of describing the present invention more clearly, and their full content is incorporated herein by reference, as if their full texts have been repeated in this document.

DETAILED DESCRIPTION

Figure 1:
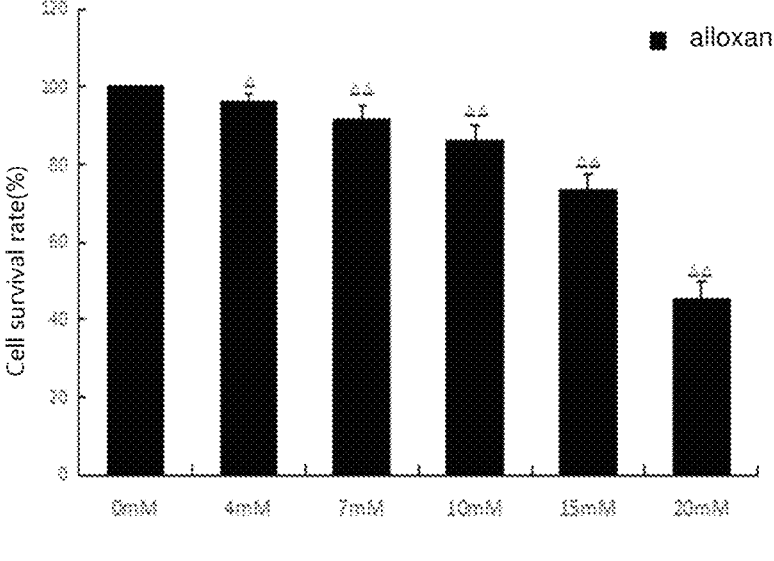
FIG. 1 shows the results of the establishment of the alloxan cell damage model, where $\Delta P < 0.05$ and $\Delta\Delta P < 0.01$, compared with the negative control group.

The following embodiments further illustrate the content of the present invention. Unless otherwise specified, the technical means used in the embodiments are conventional means well-known to those skilled in the art and commercially available common instruments and reagents, and the manufacturer's instructions for the corresponding instruments and reagents can be referred to.

Preparation Embodiment. Preparation of Mogroside Extract (60% MGV)

15 kg of fresh Corsvenor Momordica Fruit (MGV content was about 1.2%) was treated with high temperature steam, crushed with a pulverizer, and 80 L of water was added, heated to boil, filtered, and the filtrate was kept for later use. After adding 60 L of water to the filter residue, it was heated to boil, filtered, and 2 filtrates were combined; the combined filtrate was loaded on a D101 macroporous resin chromatography column equilibrated with deionized water, and first eluted with deionized water and 20% (V/V) ethanol until colorless, and then eluted with 6 times the column volume of 40% (V/V) ethanol, and the eluate was concentrated under reduced pressure until there was no alcohol; then the concentrated solution was loaded on an ADS-7 macroporous resin chromatography column equilibrated with deionized water, and eluted with 8 times the column volume of deionized water, and then eluted with 5 times the column volume of 30% (V/V) ethanol, the ethanol eluate was collected, and concentrated and dried to obtain the mogroside extract of the present invention (abbreviated as 60% MGV). The above preparation process was repeated in multiple batches, the MGV content was between 60.2 and 62.5%, and the composition was stable, all greater than 60%.

Embodiment 1. The protective effect of MG (GX008A) and NMN (GX999) on alloxan-induced β cell damage and the combination effect of the two compounds In the experiment of this embodiment, GX999 or GX008A alone and GX999 and GX008A in combination were used to evaluate the protective effects of GX999 and GX008A on alloxan-induced β cell damage. The experimental results showed that GX999 and GX008A alone had a protective effect on damaged cells within a certain concentration range. When 1 mM GX999 was combined with different concentrations of GX008A, it had a significant protective effect on damaged cells, and the combination had a synergistic protective effect.

1. Purpose of Experiment

In vitro experiments were used to study the protective effects of GX008A and GX999 on the islet β-cell damage caused by alloxan, and to explore the combination effect of the two.

2. Materials and Methods 2.1 Materials 2.1.1 Test Article

Name: Mogroside V, number GX008A, MW: 1287.44; Nicotinamide mononucleotide, number: GX999, MW: 334.22.

Source: GX008A was provided by Beijing Huibaoyuan Biotechnology Co., Ltd.; GX999 was purchased from Bontac Bio-engineering (Shenzhen) Co., Ltd.

Storage conditions: dry, protected from light, and stored at 4° C.

2.1.2 Cell Line

Rat insulinoma cells (RINm5f): purchased from the Basic Medical Cell Center, Institute of Basic Medicine, Chinese Academy of Medical Sciences.

2.1.3 Experimental Reagents

Fetal bovine serum (FBS) and RPMI1640 basal medium were purchased from GBICO, USA; Methyl thiazolyl tetrazolium (MTT), dimethyl sulfoxide (DMSO), and alloxan were purchased from Beijing Solarbio Science & Technology Co., Ltd.

2.2 Test Method

2.2.1 Cell Culture

RINm5f cells were inoculated in RPMI1640 culture medium containing penicillin, streptomycin, and 10% inactivated fetal bovine serum.

Culture was carried out at 37° C., 5% CO2, and saturated humidity, and cell growth was observed under an inverted microscope. After the cells grew to 80%-90% of the wall of the bottle, passage was performed.

2.2.2 Grouping and Treatment

RINm5F cells were cultured to the logarithmic growth phase, inoculated in 96-well culture plates at a cell density of 5×104/ml, cultured for 24 hours, and then drugs were added. The experiment was divided into a negative control group, an alloxan damage group (AXN group) and a protection group. Both the AXN group and the protection group were added with alloxan at a final concentration of 15 mM, and the protection group was added with different concentrations of GX999 and GX008A, pretreated for 1h. The experiment set up 4 duplicate wells and the experiment was repeated three times.

GX008A and GX999 were dissolved in the culture medium and freshly prepared. The final concentration was 200 mM and 500 mM.

2.2.3 Experimental Procedure

Cell Viability Assay-MTT Method:

RINm5F cells were cultured to the logarithmic growth phase, inoculated in 96-well culture plates at a cell density of 5×104/ml, cultured for 24 hours, and then drugs were added. The experiment was divided into a negative control group, an alloxan damage group (AXN group) and a protection group. Both the AXN group and the protection group were added with alloxan at a final concentration of 15 mM, and the protection group was added with different concentrations of GX999 and GX008A, pretreated for 1h. The experiment set up 4 duplicate wells and they were placed in a carbon dioxide incubator for regular culture for 24 hours. MTT 20 ul (5 mg/mL) was added to each well and incubated for 4 hours. Then the culture medium was discarded, 150 ul DMSO was added to each well and shaken for 10 minutes, and the OD value of the optical density was detected at 490 nm with a microplate reader.

CI Analysis of Drug Combination Index:

According to the inhibition rates of different concentrations of drugs alone and in combination, the Calcusyn software was used to analyze and process data such as the inhibition rates of GX999 and GX008A alone at different concentrations and the inhibition rates in combination at corresponding concentrations to obtain the combination index (CI) value. According to the definition of combination index, the synergistic effect of drugs was judged, and the synergistic effect is indicated by less than 1.0, and the antagonistic effect is indicated by greater than 1.0.

2.2.4 Statistical Methods

All experimental data were from at least 3 independent experiments and were expressed as mean±standard deviation. Statistical analysis was performed using SPSS16.0 software. Two-independent-sample t-test was used for data comparison between the two groups. One-way analysis of variance was used for data comparison between multiple groups. $P < 0.05$ was considered statistically significant.

3. Experimental Results

Establishment of Alloxan Cell Damage Model

The experiment set up a negative control group and a damage group with different concentrations of alloxan (concentrations of 4 mM, 7 mM, 10 mM, 15 mM, 20 mM), after 24 hours of exposure, then 4 duplicate wells were set up, and the MTT method was used to detect the cell survival rate. The results are shown in FIG. 1. As the concentration of the drug increased, the rate of cell damage increased, which inhibited cell proliferation in a concentration-dependent manner. Compared with the blank control group, the P value was less than 0.01, and the difference was statistically significant.

Protective Effect of GX999 Alone on Alloxan-Damaged RINm5f Cells

Figure 2:
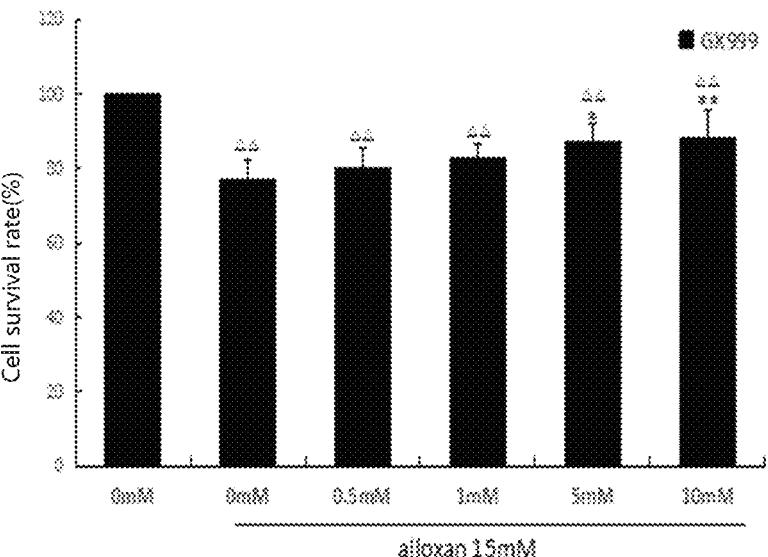
FIG. 2 shows the effect of GX999 on the survival rate of pancreatic islet cells damaged by alloxan, where, $\Delta P < 0.05$, $\Delta\Delta P < 0.01$ compared with the negative control group; *$P < 0.05$, **$P < 0.01$ compared with the alloxan damage group.

The MTT method was used to detect the effect of GX999 on the cell survival rate of alloxan-damaged pancreatic β-cells. According to the above experimental results, the concentration of alloxan was selected as 15 mM, and the experiment was divided into negative control group, alloxan damage group (AXN group) and GX999 (0.5, 1, 5, 10 mM) protection group. The results are shown in FIG. 2. Compared with the negative control group, the cell survival rate of the AXN group was significantly reduced, and the difference was statistically significant (P<0.01); after adding GX999 treatment, the cell survival rate could be significantly improved, and with the increase of the concentration of the protection group, the cell survival rate gradually increased. Compared with the AXN group, when the concentration of GX999 was 5 mM (P<0.05), 10 mM (P<0.01), the difference was statistically significant.

Analysis of the Effect of GX999 on Alloxan

Figure 3:
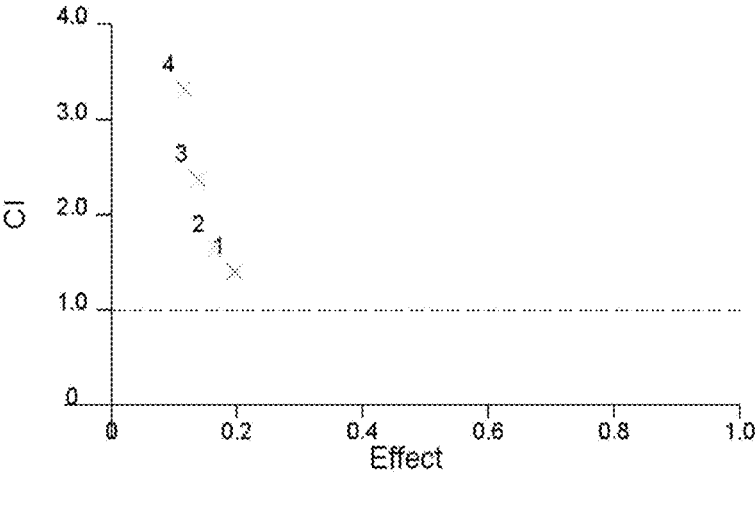
FIG. 3 shows the combination index CI value of GX999 with alloxan. 1: GX999 0.5 mM; 2: GX999 1 mM; 3: GX999 5 mM; 4: GX999 10 mM.

Calcusyn software was used for calculation, and the results are shown in FIG. 3. The CI value of GX999 with alloxan was all greater than 1.0, indicating that GX999 has an antagonistic effect on alloxan, that is, GX999 antagonizes alloxan-induced damage and plays a cytoprotective effect.

Protective Effect of GX008A Alone on Alloxan-Damaged RINm5f Cells

Figure 4:
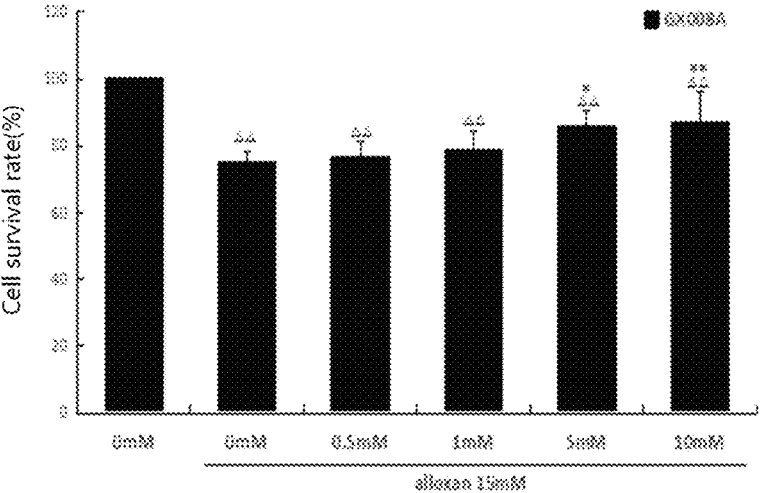
FIG. 4 shows the effect of GX008A on the survival rate of alloxan-damaged islet cells, where $\Delta P < 0.05$ and $\Delta\Delta P < 0.01$, compared with the negative control group; *$P < 0.05$, **$P < 0.01$ compared with the alloxan damage group.

The MTT method was used to detect the effect of GX008A on the cell survival rate of alloxan-damaged pancreatic β-cells. The experiment was divided into negative control group, alloxan damage group (AXN group) and GX008A (0.5, 1, 5, 10 mM) protection group. The results are shown in FIG. 4. Compared with the negative control group, the cell survival rate of the AXN group was significantly reduced, and the difference was statistically significant (P<0.01); after adding GX008A treatment, the cell survival rate could be significantly improved, and with the increase of the concentration of the protection group, the cell survival rate gradually increased. Compared with the AXN group, when the concentration of GX008A was 5 mM (P<0.05), 10 mM (P<0.01), the difference was statistically significant.

Analysis of the Effect of GX008A on Alloxan

Figure 5:
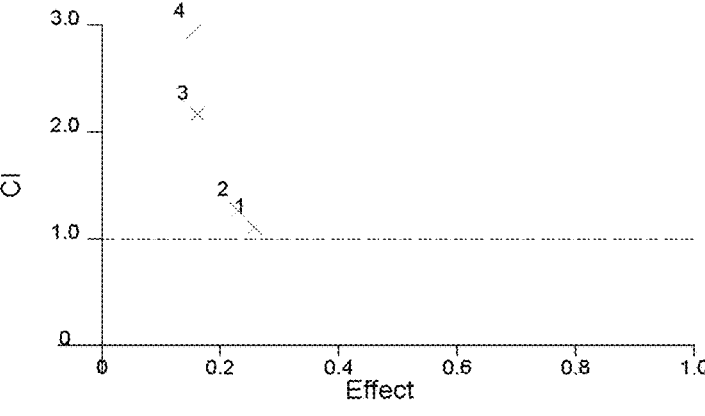
FIG. 5 shows the combination index CI value of GX008A with alloxan, wherein 1: GX008A 0.5 mM; 2: GX008A 1 mM; 3: GX008A 5 mM; 4: GX008A 10 mM.

Calcusyn software was used for calculation, and the results are shown in FIG. 5. The CI value of GX008A with alloxan was all greater than 1.0, indicating that GX008A has an antagonistic effect on alloxan, that is, GX008A antagonizes alloxan-induced damage and plays a cytoprotective effect.

Figure 6:
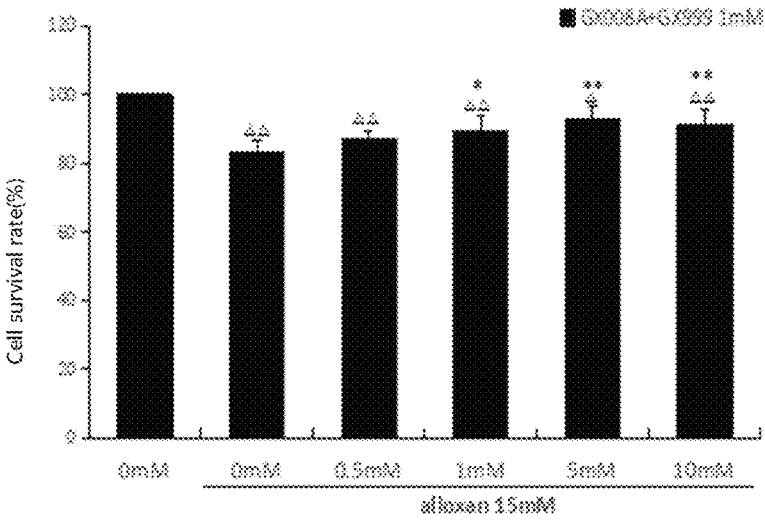
FIG. 6 shows the effect of GX999 1 mM in combination with GX008A on the survival rate of alloxan-damaged islet cells, where $\Delta P < 0.05$ and $\Delta\Delta P < 0.01$, compared with the negative control group; *$P < 0.05$, **$P < 0.01$ compared with the alloxan damage group.

Protective Effect of GX008A/GX999 Combination Application on Alloxan-Damaged RINm5f Cells MTT method was used to detect the effect of GX008A/GX999 combination application on the cell survival rate of alloxan-damaged pancreatic β-cells. The experiment was divided into negative control group, alloxan damage group (AXN group) and GX999 (1 mM) combined with GX008A (0.5, 1, 5, 10 mM) protection group. The results are shown in FIG. 6. Compared with the negative control group, the cell survival rate of the AXN group was significantly reduced, and the difference was statistically significant (P<0.01); the combination protection group could increase the survival rate of the cells and with the increase of the concentration, the cell survival rate gradually increased. Compared with the AXN group, the differences with GX999 (1 mM) combined with GX008A 1 mM (P<0.05), 5 mM and 10 mM (P<0.01) were statistically significant.

Analysis of the Combination Effect of GX008A/GX999

Figure 7:
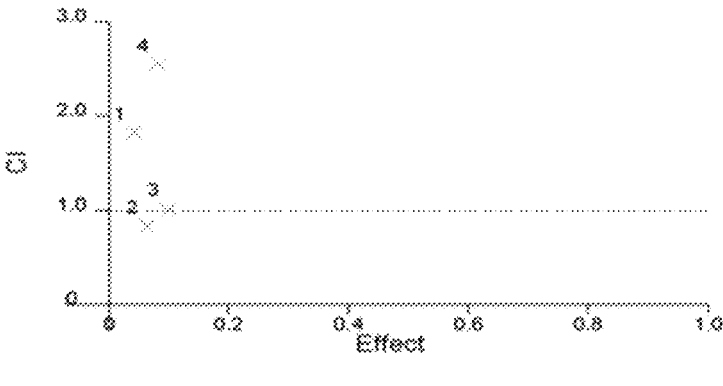
FIG. 7 shows the CI value of the combination index of GX008A/GX999 to alloxan, where 1: GX008A 0.5 mM+GX999 1 mM; 2: GX008A 1 mM+GX999 1 mM; 3: GX008A 5 mM+GX999 1 mM; 4: GX008A 10 mM+GX999 1 mM.

The combination application efficiency was calculated using Calcusyn software. The results are shown in FIG. 7. When the combination protection group was compared with the single-drug protection group, drug combination index CI of GX999 (1 mM) combined with GX008A 1 mM, 5 mM<1.0, suggesting that GX999 and GX008A have a synergistic protective effect on alloxan-induced damage.

4. Experimental Conclusion

The experimental results showed that GX999 and GX008A alone had a protective effect on damaged cells within a certain concentration range. When 1 mM GX999 was combined with different concentrations of GX008A, it had a significant protective effect on damaged cells, and the combination had a synergistic protective effect.

Embodiment 2. The effect of mogroside (MG, GX008A) and nicotinamide mononucleotide (NMN, GX999) on the differentiation of 3T3-L1 preadipocytes and the combination effect of the two compounds The experiment of this embodiment used GX999 or GX008A alone, and GX999 and GX008A in combination to evaluate the effects of GX999 and GX008A on the proliferation of preadipocytes. The experimental results showed that GX999 and GX008A can inhibit the proliferation of 3T3L1 adipocytes with a concentration-dependent effect. The combination application of the two drugs can synergistically inhibit cell proliferation; GX999 and GX008A can significantly inhibit the adipogenesis of adipocytes, and the combination application can synergistically inhibit adipogenesis to a certain extent, that is, the combination application has a synergistic inhibitory effect on the differentiation of 3T3L1 preadipocytes.

1. Purpose of Experiment

To study the effects of GX008A and GX999 on the proliferation and differentiation of 3T3-L1 preadipocytes, and observe the combination effect of the two compounds.

2. Materials and Methods 2.1 Materials 2.1.1 Test Article

Same as embodiment 1.

2.1.2 Cell Line

3T3-L1 cell line: purchased from the Basic Medical Cell Center, Institute of Basic Medicine, Chinese Academy of Medical Sciences.

2.1.3 Experimental Reagents

Calf calf serum (CS), fetal bovine serum (FBS), and DMEM basal medium were purchased from GBICO, USA; IBMX, dexamethasone, and insulin were purchased from SIGMA, USA; oil red O powder, tetramethylazazole blue (MTT) was purchased from Beijing Solarbio Science & Technology Co., Ltd.

2.2 Test Method 2.2.1 Cell Culture

3T3L1 cells were placed in DMEM high-glucose medium containing 10% calf serum and cultured at 37° C. and 5% $CO_2$. When the cells reached 90% confluence, they were digested with 0.25% trypsin, passaged, and inoculated in a 96-well cell culture plate.

2.2.2 Grouping and Treatment

GX008A and GX999 were dissolved in the culture medium and freshly prepared. The final concentration was 200 mM and 500 mM.

2.2.3 Experimental Procedure

Cell Viability Assay-MTT Method:

The logarithmic growth phase cells were taken and inoculated in a 96-well plate at a density of 5×103 cells/mL, with 4 replicate wells in each group. After the cells grew to about 40%-50% confluence, the fresh drug-containing medium was replaced with and they were divided into a GX999 alone group, a GX008A group, and a GX999+GX008A combination group. After culturing for 48h, MTT 20 ul (5 mg/mL) was added to each well and incubated for 4h. Then the culture medium was discarded, 150 ul DMSO was added to each well and shaken for 10 minutes, and the OD value of the optical density was detected at 490 nm with a microplate reader, and the cell survival rate was calculated according to the formula. Analysis of drug synergy:

Combination method: 10 mM GX999 in combination with GX008A (0, 5, 10, 30, 50 mM) group. According to the inhibition rates of different concentrations of drugs alone and in combination, the Calcusyn software was used to analyze and process data such as the inhibition rates of GX999 and GX008A alone at different concentrations and the inhibition rates in combination at corresponding concentrations to obtain the combination index (CI) value. According to the definition of combination index, the synergistic effect of drugs was judged, and the synergistic effect is indicated by less than 1.0, and the antagonistic effect is indicated by greater than 1.0.

Induction of Differentiation Experiment of Adipocytes:

2 days after the 3T3-L1 preadipocytes grew to complete confluence, the induction of differentiation began. That is, the DMEM complete medium was discarded, and replaced with DMEM complete medium containing 5 ug/ml insulin, 0.5 mM IBMX, 1 uM dexamethasone, and after 2 days, it was replaced with DMEM complete culture medium containing 5 ug/ml insulin and cultured for 2 days. Then DMEM complete culture medium was used to continue culturing for 2 days. From the first day of differentiation, the experimental group was given a culture medium containing 10 mM GX999 or 10 mM GX008A to intervene in the whole process of cell differentiation, and the control group was added with conventional inducers.

Oil Red O Staining:

After 8 days of induced differentiation, the cells were fixed with 4% paraformaldehyde for 30 minutes, washed 3 times with balanced salt solution (PBS), incubated with oil red O staining solution for 60 minutes, the pipetted liquid was rinsed 3 times with PBS, and observed for the formation of lipid droplets under an inverted microscope and a video was taken. Isopropanol (200 ul per well) was added, and the absorbance at A490 nm was measured with a microplate reader after 5 minutes.

2.2.4 Statistical Methods

All experimental data were from at least 3 independent experiments and were expressed as mean±standard deviation. Statistical analysis was performed using SPSS16.0 software. Two-independent-sample t-test was used for data comparison between the two groups. One-way analysis of variance was used for data comparison between multiple groups. P<0.05 was considered statistically significant.

3. Experimental Results

The Effect of GX999 on the Proliferation of 3T3L1 Preadipocytes

Figure 8:
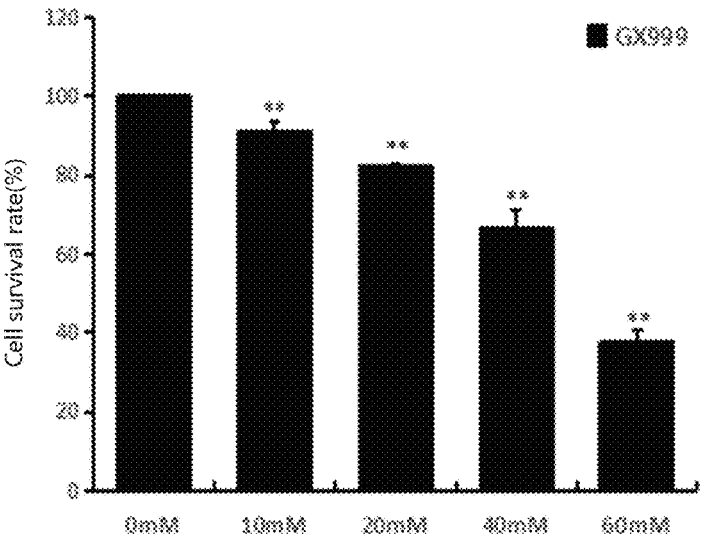
FIG. 8 shows the effect of GX999 on the survival rate of 3T3L1 cells, where *$P < 0.05$ and **$P < 0.01$, compared with the negative control group.
Figure 9:
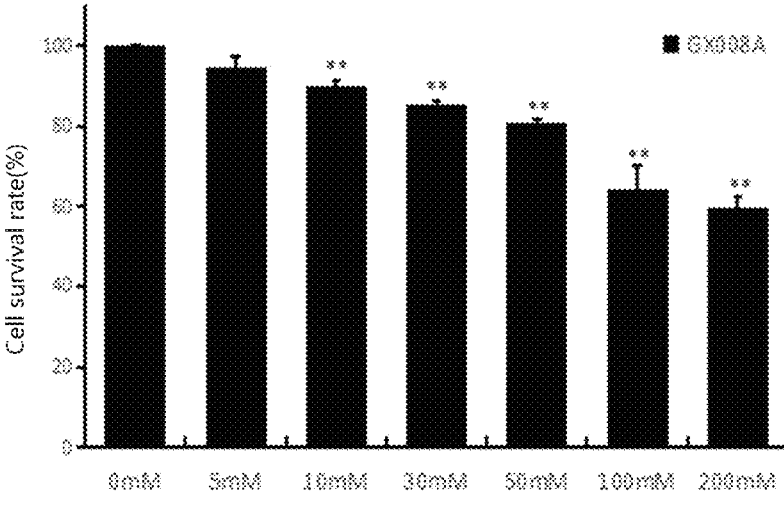
FIG. 9 shows the effect of GX008A on the survival rate of 3T3L1 cells, where *$P < 0.05$ and $P < 0.01$, compared with the negative control group

The MTT method was used to detect the cell survival rate. The results are shown in FIG. 8. When GX999 (0, 10, 20, 40, 60 mM) was used alone to treat 3T3L1 cells for 48 hours, as the drug concentration increased, the survival rate of 3T3L1 cells decreased, and it inhibited cell proliferation in a concentration-dependent manner. Compared with the blank control group, the P values were all less than 0.01, and the differences were statistically significant. According to the above inhibition rate, the IC50 of GX999 was 51.7±1.5 mM. The Effect of GX008A on the Proliferation of 3T3L1 Preadipocytes The results are shown in FIG. 9. When GX008A (0, 5, 10, 30, 50, 100, 200 mM) was used alone to treat 3T3L1 cells for 48 hours, as the drug concentration increased, the survival rate of 3T3L1 cells decreased, and it inhibited cell proliferation in a concentration-dependent manner. Compared with the blank control group, the P values were all less than 0.01, and the differences were statistically significant.

Figure 10:
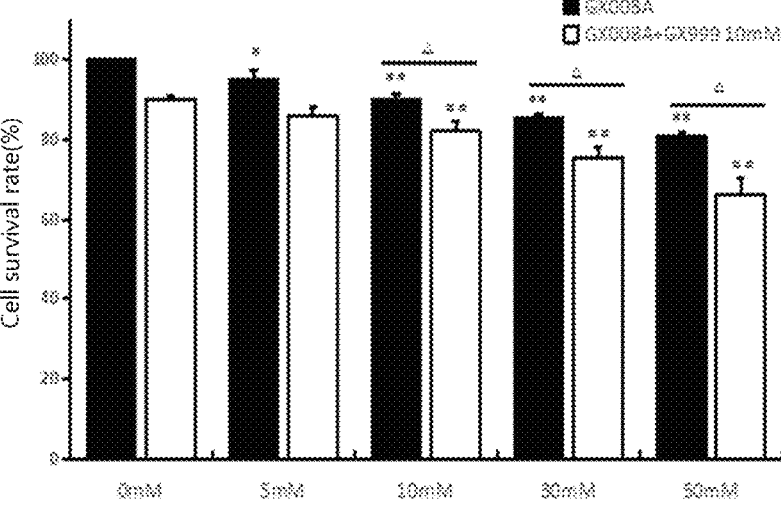
FIG. 10** shows the effect of the combination of GX008A/GX999 on the survival rate of 3T3L1 cells, where *$P < 0.05$, **$P < 0.01$ compared with the negative control group; #$P < 0.05$, ##$P < 0.01$ compared with 10 mM GX999 group; $\Delta P < 0.05$ compared with GX008A alone group.

The Effect of GX008A Combined with GX999 on the Proliferation of 3T3L1 Preadipocytes When GX008A and GX999 acted alone, with the increase of the concentration of administration, the growth inhibitory effect on 3T3L1 preadipocytes also gradually increased, showing an obvious dose-dependent effect relationship. When 10 mM GX999 was used in combination with different concentrations of GX008A (0, 5, 10, 30, 50 mM), the results are shown in FIG. 10 (only part of data in the GX008A alone group shown in FIG. 9 is listed for visual comparison). With the increase of the concentration of GX008A, the combination inhibitory effect of the two showed an increasing trend; compared with the single-agent group, the inhibitory effect of GX999 combined with GX008A 10, 30, and 50 mM was significantly greater than that of the 10 mM GX999 group (P<0.01) and GX008A alone group (P<0.05).

Figure 11:
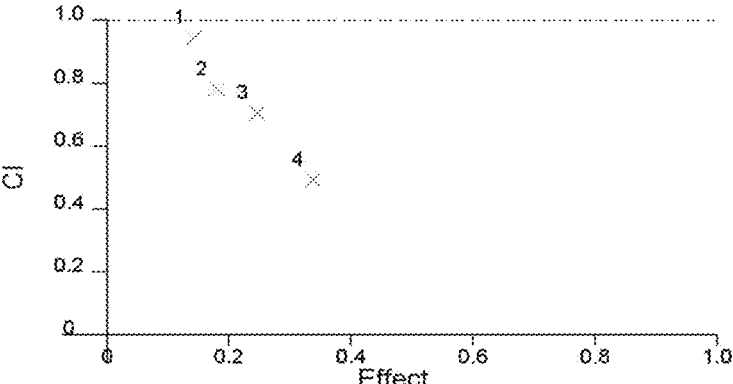
FIG. 11 shows the CI value of the GX008A/GX999 combination index, where 1: 5 mM GX008A+10 mM GX999, 2: 10 mM GX008A+10 mM GX999, 3: 30 mM GX008A+10 mM GX999, 4: 50 mM GX008A+10 mM GX999.

Synergy Analysis of 10 mM GX999 Combined with GX008A:

Using Calcusyn software for calculation, the results are shown in FIG. 11. The CI values of 10 mM GX999 combined with GX008A were all less than 1.0, suggesting that the combination of the two drugs has a synergistic effect. GX008A can have a synergy with GX999 to inhibit the growth of 3T3L1 preadipocytes to a certain extent.

Effect of GX999/GX008A on the Differentiation of Preadipocytes

Figure 12:
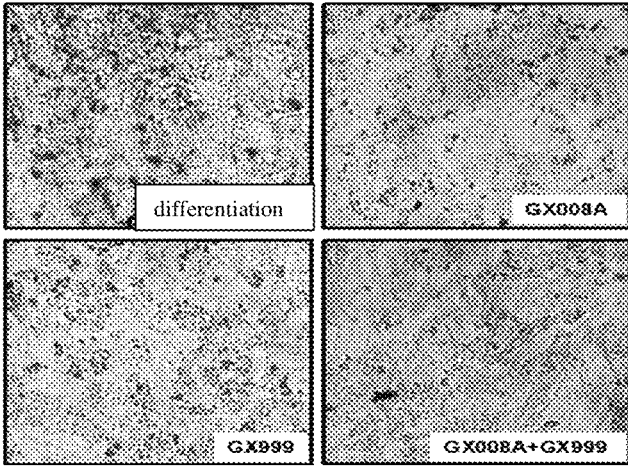
FIG. 12 shows the effect of GX999/GX008A on the differentiation of 3T3L1 cells.
Figure 13:
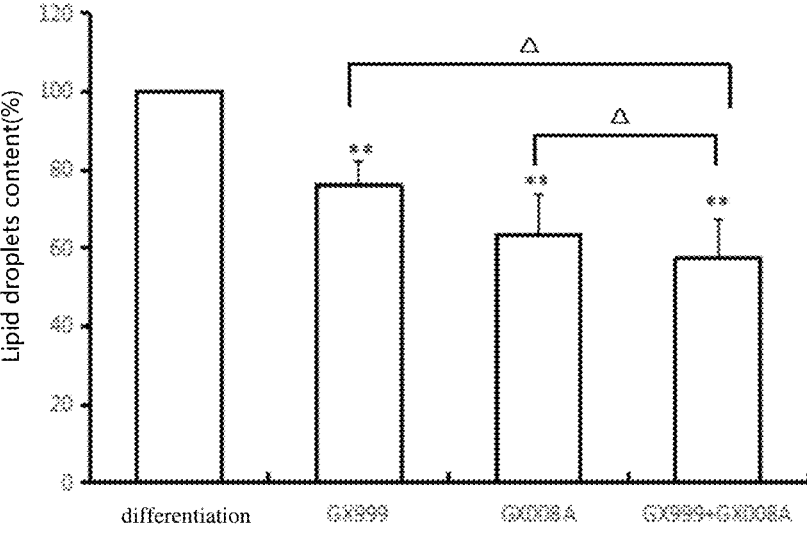
FIG. 13 shows the effect of GX008A/GX999 on the differentiation of 3T3L1 cells, where *$P < 0.05$, **$P < 0.01$ compared with the differentiation group; $\Delta P < 0.05$ compared with the GX999/GX008A alone group.

Based on the results of the above-mentioned combination application experiment, the drug concentration and combination concentration were selected. During the induction of differentiation, 10 mM GX999, 10 mM GX008A, 10 mM GX999+10 mM GX008A were added and treated for 8 days, stained with Oil Red 0, observed and photographed under a microscope, and Oil Red 0 was extracted with isopropanol, the OD value was read. FIG. 12 shows exemplary photos of each group. FIG. 13 shows the quantitative lipid droplet content, indicating that GX999 and GX008A alone or in combination can inhibit adipogenesis. Compared with the differentiation group, the lipid droplet content in cells was significantly reduced (P<0.01); the lipid droplet content of the GX008A/GX999 combination group was significantly lower than that of the single-agent group (P<0.05).

4. Experimental Conclusion

The experimental results indicated that: GX999 and GX008A can inhibit the proliferation of 3T3L1 adipocytes with a concentration-dependent effect. The combination application of the two drugs can synergistically inhibit cell proliferation; GX999 and GX008A can significantly inhibit the adipogenesis of adipocytes, and the combination application can synergistically inhibit adipogenesis to a certain extent, that is, the combination application has a synergistic inhibitory effect on the differentiation of 3T3L1 preadipocytes.

Embodiment 3. Hypoglycemic effect of mogroside (60% MGV) and nicotinamide mononucleotide (NMN, GX999)

1. Preparation of Test Samples
(1) Preparation of NMNMG200
  20 g of NMN (purity 98%) and 0.5 g of 60% MGV (prepared in the foregoing preparation embodiment) were dissolved into 100 ml of an aqueous solution containing 10% glycerol to prepare NMNMG200.
(2) Preparation of NMN200
  20 grams of NMN (98% purity) was dissolved into 100 ml of 10% glycerin-containing aqueous solution to prepare NMN200.
(3) Preparation of MG5
  0.5 g of 60% MGV (prepared in the foregoing preparation embodiment) was dissolved into 100 ml of 10% glycerin-containing aqueous solution to prepare MG5.

2. Blood Glucose Effect Test Before Lunch

Volunteers with pre-meal blood glucose>6.0 in the morning were tested for fasting blood glucose (Om) every morning, and then they took 1 ml of NMNMG200, NMN200 or MG5 prepared in embodiment 1; method of administration: 1 ml of the solution was added into 100 ml of drinking water and was drunk by them and then the blood glucose levels for 30 minutes (30 min) and 60 minutes (60 min) were measured respectively. The results are shown in Table 1:

TABLE 1

Tests of blood glucose levels of volunteers taking different samples

| Sample name | Number within the group | Gender | Age | Administration at 0 min | Administration at 30 min | Administration at 60 min |
|---|---|---|---|---|---|---|
| NMNMG200 | 001 | 男 | 60 | 6.6 | 6.3 | 6.3 |
| | 002 | 男 | 61 | 6.5 | 6.1 | 6.0 |
| | 003 | 男 | 60 | 6.3 | 5.9 | 5.9 |
| NMN200 | 001 | 男 | 60 | 6.3 | 6.3 | 6.5 |
| | 002 | 男 | 63 | 6.6 | 6.5 | 6.5 |
| | 003 | 男 | 60 | 7.2 | 7.1 | 7.1 |
| | 004 | 女 | 50 | 5.9 | 6.3 | 6.6 |
| MG5 | 001 | 男 | 60 | 6.2 | 6.2 | 6.2 |
| | 002 | 女 | 63 | 6.5 | 6.5 | 6.5 |
| | 003 | 女 | 63 | 6.7 | 6.7 | 6.7 |

As described in the above experimental procedure, the volunteers with the usual blood glucose before meals in the morning>6.0 were chosen to test the pre-meal fasting blood glucose in the morning. The time of taking NMNMG200 was about 1 hour before going to bed every night, and the blood glucose level was tested after taking it. The results are shown in Table 2: Table 2 Test results of blood glucose levels of volunteers before and after taking NMNMG200

| Volunteer Number | Gender | Before administration | After administration |
|---|---|---|---|
| 001 | Male | 6.3 | 4.8 |
| 002 | Male | 6.5 | 5.4 |
| 003 | Male | 6.7 | 5.6 |
| 004 | Male | 6.6 | 5.2 |

The results show that the combined use of mogroside and nicotinamide mononucleotide has the effect of lowering blood glucose.

The invention claimed is:

1. A pharmaceutical composition comprising nicotinamide mononucleotide and mogroside, wherein the molar ratio of nicotinamide mononucleotide:mogroside is 1-2:1-5;

mogroside is mogroside V or a Corsvenor Momordica Fruit extract containing mogroside V; and the method for extracting mogroside includes the following steps:

(1) Corsvenor Momordica Fruit is extracted by heating with water and filtered;

(2) the filtrate obtained in step (1) is purified with a D101 macroporous resin chromatography column, and the eluent eluted with 35-45% (V/V) ethanol is collected and concentrated; and (3) the concentrated solution obtained in step (2) is purified with an ADS-7 macroporous resin chromatography column, and the eluate eluted with 25-35% (V/V) ethanol is collected and concentrated to dryness.

2. The composition according to claim 1, wherein the content of mogroside V in the said extract is not less than 30% (w/w).

3. The composition according to claim 1, wherein the content of mogroside V in the said extract is not less than 60% (w/w).

4. A preparation method of the pharmaceutical composition according to claim 1, comprising the step of mixing nicotinamide mononucleotide and mogroside.

5. The method of claim 4, comprising an extraction method of mogroside, which comprises the following steps:

(1) Corsvenor Momordica Fruit is extracted by heating with water and filtered;

(2) the filtrate obtained in step (1) is purified with a D101 macroporous resin chromatography column, and the eluent eluted with 35-45% (V/V) ethanol is collected and concentrated; and (3) the concentrated solution obtained in step (2) is purified with an ADS-7 macroporous resin chromatography column, and the eluate eluted with 25-35% (V/V) ethanol is collected and concentrated to dryness.

6. A pharmaceutical preparation, comprising the pharmaceutical composition according to claim 1, and pharmaceutically acceptable excipients.

7. The pharmaceutical preparation of claim 6, wherein the preparation is a granule.

8. A method comprising administering a pharmaceutical preparation containing the pharmaceutical composition according to claim 1 for reducing blood glucose, promoting the growth and repair of pancreatic islet cells, preventing and treating hyperglycemia, and/or preventing and treating diabetes.

9. A method comprising administering a pharmaceutical preparation comprising the pharmaceutical composition according to claim 1 for controlling fat accumulation and body weight, preventing and treating hyperlipidemia, and/or preventing and treating cardiovascular diseases.

10. A health food composition comprising nicotinamide mononucleotide and mogroside, wherein the molar ratio of nicotinamide mononucleotide:mogroside is 1-2:1-5;

mogroside is mogroside V or a Corsvenor Momordica Fruit extract containing mogroside V; and the method for extracting mogroside includes the following steps:

(1) Corsvenor Momordica Fruit is extracted by heating with water and filtered;

(2) the filtrate obtained in step (1) is purified with a D101 macroporous resin chromatography column, and the eluent eluted with 35-45% (V/V) ethanol is collected and concentrated; and (3) the concentrated solution obtained in step (2) is purified with an ADS-7 macroporous resin chromatography column, and the eluate eluted with 25-35% (V/V) ethanol is collected and concentrated to dryness.

11. The composition according to claim 10, wherein the content of mogroside V in the said extract is not less than 30% (w/w).

12. The composition according to claim 10, wherein the content of mogroside V in the extract is not less than 60% (w/w).

13. A preparation method of the health food composition according to claim 10, comprising the step of mixing nicotinamide mononucleotide and mogroside.

14. The method according to claim 13, further comprising an extraction method of mogroside, which comprises the following steps:

(1) Corsvenor Momordica Fruit is extracted by heating with water and filtered;

(2) the filtrate obtained in step (1) is purified with a D101 macroporous resin chromatography column, and the eluent eluted with 35-45% (V/V) ethanol is collected and concentrated; and (3) the concentrated solution obtained in step (2) is purified with an ADS-7 macroporous resin chromatography column, and the eluate eluted with 25-35% (V/V) ethanol is collected and concentrated to dryness.

15. A health food, comprising the health food composition according to claim 10, and food acceptable excipients.

16. The health food of claim 15 wherein the health food is a dairy product, a beverage or a biscuit.

17. The composition according to claim 1, wherein the composition is in a form selected from the group consisting of tablets, pills, capsules, powders, suspensions, granules, syrups, emulsions, suspension liquids and combinations thereof.

* * * * *